United States Patent [19]

Heilman

[11] 3,957,831
[45] May 18, 1976

[54] PREPARATION OF GLYCIDYL ESTERS OF UNSATURATED ACIDS

[75] Inventor: William J. Heilman, Allison Park, Pa.

[73] Assignee: Gulf Research & Development Company, Pittsburgh, Pa.

[22] Filed: Jan. 27, 1970

[21] Appl. No.: 6,279

Related U.S. Application Data

[63] Continuation-in-part of Ser. No. 704,230, Feb. 9, 1968, abandoned.

[52] U.S. Cl. .............................................. 260/348 A
[51] Int. Cl.² ...................................... C07D 301/30
[58] Field of Search ............................... 260/348 A

[56] References Cited
UNITED STATES PATENTS

| | | | |
|---|---|---|---|
| 2,448,602 | 9/1948 | Kester et al. | 260/348 |
| 2,537,981 | 1/1951 | Edwards | 260/348 |

FOREIGN PATENTS OR APPLICATIONS

| | | | |
|---|---|---|---|
| 40-7887 | 4/1965 | Japan | 260/348 A |
| 1,446,544 | 6/1966 | France | 260/348 |

OTHER PUBLICATIONS

Kester et al., Jour. Organic Chemistry, Vol. 8 (1943) pp. 550–556.

*Primary Examiner*—Norma S. Milestone

[57] ABSTRACT

A glycidyl ester, such as glycidyl methacrylate, is prepared by contacting an unsaturated fatty acid, such as methacrylic acid, with an alkali metal base in a first reaction zone to form an alkali metal salt, such as sodium methacrylate, in the presence of a solvent which will azeotrope with water and which is free of epoxide groups. Substantially all of the water is removed from the first reaction zone by, for example, removing a water-solvent azeotrope and, optionally, at least a portion of the solvent is removed. The alkali metal salt admixed with or suspended in at least a portion of the solvent is then contacted with a solid particulate drying agent free of halogen atoms and is thereafter reacted in a second reaction zone in the absence of the drying agent with dry epichlorohydrin under substantially anhydrous conditions to form the desired glycidyl ester. Optionally, the drying agent can remain in the second reaction zone provided said drying agent is such that it either reacts with water to form a hydrate or hydroxide or is a zeolite material having an average pore diameter less than six degrees Angstrom (°A.).

2 Claims, No Drawings

PREPARATION OF GLYCIDYL ESTERS OF UNSATURATED ACIDS

This application is a continuation-in-part of our co-pending Ser. No. 704,230, filed February 9, 1968, now abandoned, and assigned to the same assignee as the present application.

This invention relates to a process for the preparation of glycidyl esters of unsaturated acids, and in particular to the preparation of glcyidyl methacrylate.

Prior art processes for the preparation of glycidyl esters, such as the preparation of glycidyl methacrylate, by the reaction of epichlorohydrin with unsaturated acids or alkali metal salts thereof suffer from either or both of (1) poor yields of the glycidyl ester based on the unsaturated acid or alkali metal salt thereof or (2) poor desired ester product purity due to the formation of unwanted by-products. In addition, the prior art is contradictory in its teachings regarding the use of aqueous or anhydrous conditions in the preparation of the esters. For example, U.S. Pat. No. 2,893,875 teaches the use of aqueous media to prepare fatty acid-epichlorohydrin adducts. Similarly, U.S. Pat. No. 2,524,432 teaches the esterification of an epoxy compound such as epichlorohydrin with an alpha,beta-ethylenically unsaturated monocarboxylic acid or the ester forming derivative of such acid in the presence of a water medium. Contrariwise, U.S. Pat. No. 2,537,981 to Edwards teaches the preparation of an alkali metal salt of a fatty acid which is then filtered and dried before reaction with the epichorohydrin. All of the working examples in the Edwards patent utilize the dry salt for reaction with the epichlorohydrin.

Possibly to avoid some of the above confusion, other art, U.S. Pat. No. 3,075,999, teaches a one step process for the preparation of a glycidyl ester wherein a fatty acid, epichlorohydrin, aqueous alkali metal salt and a quaternary ammonium halide catalyst are admixed and reacted at elevated temperatures in excess of 70°C.

A more recently issued Japanese Patent No. 40-7887 teaches a three step process for the preparation of glycidyl methacrylate. Initially, methacrylic acid is neutralized in a solvent and in the presence of a polymerization preventative agent, such as phenyl (alpha) naphthyl amine. Secondly, the product is dehydrated by azeotropic distillation. Epichlorohydrin is then added together with a known catalyst to promote the reaction between the formed salt and the epichlorohydrin. The Japanese patent teaches it has been customary to treat the unsaturated organic acid with an aqueous alkali solution, thereby converting it into a unsaturated organic acid salt, followed by the concentration of the same to make a gruel-like substance which is dried under a reduced pressure for a long period of time before it is reacted with epichlorohydrin. The Japanese process improves product purity somewhat but the yields of glycidyl methcrylate are lower than desired.

French Pat. No. 1,446,544 defines a process for the preparation of esters by the reaction of salts (soaps) of carboxylic acids with epoxy-halogeno-alkanes, the process being characterized in that these salts are made to react in the form of suspensions in organic solvents; which have been obtained by progressively adding aqueous solutions of hydroxides to solutions of these carboxylic acids in organic solvents, water having been driven off by distillation.

Thus, it appears that investigations have been made into single and multi-step processes, either aqueous or partially non-aqueous systems for the preparation of glycidyl esters. Despite the various processes and approaches which have been tried, problems are still prevalent as noted above. The yields of glycidyl methacrylate are reduced by the formation of by-products such as a chlorohydrin ester

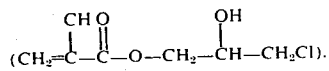

The purity of the desired glycidyl methacrylate is reduced by the presence of this chlorohydrin ester and by the presence of an undesired by-product, 1,3-dichloropropanol-2. The process of this invention results in both increased yields of glycidyl methacrylate based on the alkali metal acid salt and in improved purity of the glycidyl methacrylate.

In view of the conflicting and divergent methods of approach taken by various persons supposedly skilled in the art to the basic problem or preparing the glycidyl esters in high yield, it was surprising to discover tht glycidyl esters can be made in very high yields, in many instances over 90 percent of theoretical, by a careful control of process parameters not heretofore taught and appreciated as being critical in achieving the desired results.

In accordance with the invention, a glycidyl ester is prepared by a process which comprises:

reacting an solvent fatty acid having from three to 20 carbon atoms with an alkali metal base to form an alkali metal salt of said acid and water in a first reaction zone in the presence of an epoxide-free solent which will azeotrope with water;

removing substantially all of the water from said first reaction zone and, optionally, a portion of the solvent, to form a first reaction zone product slurry;

contacting said first reaction zone product slurry with a solid particulate drying agent free of halogen atoms;

and thereafter reacting said slurry in the absence of said drying agent in a second reaction zone with dry epichlorohydrin under substantially anhydrous conditions to form the desired glycidyl ester;

with the option that said drying agent can remain in said second reaction zone provided said drying agent is such that it either reacts with water to form an hydroxide or hydrate or is a zeolite having an average pore diameter less than six degrees Angstrom (°A.).

The glycidyl esters of the present invention are glycidyl esters of unsaturated monocarboxylic aliphatic organic acids having from three to 20 carbon atoms per molecule, i.e., fatty acids having from three to 20 carbon atoms. These glycidyl esters may be represented by the general Formula I below:

FORMULA I

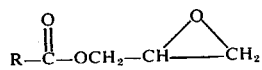

wherein R is an unsaturated unsubstituted alkyl radical having from two to 19 carbon atoms.

The glycidyl esters of the unsaturated fatty acids of the present invention are obtained by reaction of an alkali metal salt of an unsaturated fatty acid, for example, methacrylic acid, with epichlorohydrin.

The suitable unsaturated fatty acids comprise the acids represented by the general Formula II below:

FORMULA II

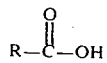

two to R is an unsaturated unsubstituted alkyl radical having from two to 19 carbon atoms, preferably from two to ten carbon atoms, and most preferably having from two to four carbon atoms. By an "unsaturated unsubstituted alkyl radical" is meant an alkyl radical or group containing only carbon and hydrogen and having one or two, preferably one, olefinic double bond.

Examples of suitable unsaturated fatty acids coming within the above formula include acrylic; methacrylic; allylacetic; vinylacetic; crotonic; isocrotonic; tiglic; angelic; senecioic; hexenic acids ($C_5H_9COOH$); hypogeic acid ($C_{15}H_{29}COOH$); oleic; elaidic acid ($C_{17}H_{33}COOH$); linoleic acid ($C_{18}H_{32}O_2$); palmitoleic acid ($C_{16}H_{30}O_2$); myristoleic acid ($C_{14}H_{26}O_2$); and linolenic acid ($C_{18}H_{30}O_2$).

The above-described unsaturated fatty acids are reacted in a first reaction zone or stage with an alkali metal base. By an "alkali metal base" is meant an alkali metal hydroxide or carbonate which will enter into a neutralization reaction with an acid to form the salt of the acid plus water. The base, if a carbonate, can be used in the solid form but is preferably in solution in an alcohol or water. The alkali metal hydroxides are used in solution only. By an "alkali metal" is meant sodium, potassium, lithium or cesium.

The preferred bases are the alkali metal hydroxides which can be represented by Formula III below:

FORMULA III

MOH where M represents any alkali metal selected from the group consisting of sodium, potassium, lithium and cesium. It has been found that solid dry alkali metal hydroxides do not work in the process of this invention even when ground up in fine powdered form. Apparently the solid alkali metal hydroxide is not soluble in the unsaturated fatty acid, and thus the desired reaction does not occur. It is necessary, therefore, to employ a solution of the alkali metal hydroxide in a suitable solvent, such as water, or a low boiling alcohol, such as methanol, which boils lower than the solvent employed and can suitably be removed from the reaction product before the epichlorohydrin is added in the second stage. Water is the preferred solvent for the alkali metal hydroxide. The amount of water necessary to form an aqueous solution is not critical, but sufficient water or other solubilizing agent should be employed to keep the alkali metal hydroxide in solution. Commercially available 50 to 70 percent aqueous solutions of alkali metal hydroxides, such as sodium hydroxide and potassium hydroxide, can suitably be employed and are, of course, the most desired since they are easily obtained.

Theoretically, one mole of the alkali metal base is required per mole of the unsaturated fatty acid in order to produce one mole of the alkali metal carboxylate. For economic reasons, the molar ratio of the alkali metal to the unsaturated monocarboxylic acid should be about 1:1. It is preferably between 0.95:1 and 1.5:1 and is more preferably between 0.98:1 and 1.2:1. Higher amounts of alkali metal hydroxide, i.e., in molar ratios up to 5:1 can be employed but offer little advantage. Lower amounts of alkali metal hydroxide, i.e., in molar ratios below about 0.8:1, can be employed but are not preferred.

The reaction in the first reaction zone or stage is a simple neutralization reaction with the formation of a salt and water in accordance with the following equation:

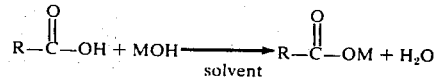

where M and R have the significance defined above. The

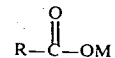

salt is a solid which precipitates in finely divided form and can be suspended by suitable agitation in the solvent. As noted above, the solvent may be any epoxide-free liquid material which will form an azeotrope with water and which, of course, is substantially unreactive with the components of the reaction mixture under the conditions of the reaction. The solvents must also be inert with respect to epichlorohydrin since epichlorohydrin is employed as the charge stock in the second stage of the reaction. By "inert" is meant that it will nt chemically react with the components of the reaction mixture or epichlorohydrin under the conditions of the reaction. Epichlorohydrin is a liquid material which forms an azeotrope with water but is not a suitable solvent for the first stage reaction since the epoxide group tends to interact with the water at least in part to form unwanted side reaction products. It has been found that inert solvents can be employed as a reaction medium in the formation of the alkali metal salts and the same solvents can be used to aid in the removal of water by azeotropic distillation while maintaining the salts in a slurry suspension. In addition, the solvents may serve as a reaction medium for the formation of the desired glycidyl esters upon the addition of the epichlorohydrin and, preferably, a catalyst.

Suitable solvents include benzene, toluene and other low boiling alkylated aromatic hydrocarbons; halogenated hydrocarbons such as carbon tetrachloride and 1,2-dichloroethane; 1,2-dichloropropane; trichloroethylene; and 2-chloropropane. A more detailed list of suitable solvents will be given below. Any chemist with ordinary skill in the art would known which materials azeotrope with water and which do not adversely react in either step of the process of this invention. The more preferred solvents are those which form azeotropes having the larger weight percents of water so that lesser amounts of the solvent-water azeotrope need to be removed overhead in a distillation zone to substantially dry the reaction mixture. It is also preferred to employ those solvents which, although they form an azeotrope with water, are also substantially insoluble in water to allow the solvent removed overhead as an azeotrope to be physically separated from the water and recycled to the reaction zone. It is further preferred that the solvent not boil too close to epichlorohydrin from which it is preferably distilled after the formation of the desired glycidyl esters.

The more preferred solvents can be represented by the general Formula IV below:

FORMULA IV

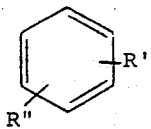

where R' and R'' are the same or different and are selected from the class consisting of hydrogen, alkyl groups having from one to two carbon atoms, chlorine, bromine and iodine.

Another preferred group of solvents can be represented by the general Formula V below:

FORMULA V

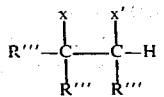

where $x$ and $x'$ can be the same or different and are selected from the groups consisting of chlorine, bromine and iodine and R''' is selected from the group consisting of hydrogen, alkyl radicals having from one to two carbon atoms, chlorine, bromine or iodine.

A sufficient amount of the solvent should be employed to allow the solvent to serve its function of maintaining the alkali metal salt of the unsaturated fatty acid in suspension before, during and after removal of the water from the reaction zone. The molar ratio of the solvent to the unsaturated fatty acid in the first step is greater than 1:1, and is usually on the order of 5:1. Much greater amounts of solvent to acid, for example on the order of 10:1 or 100:1 or greater, e.g., 1000:1 or higher, can also, of course, be employed.

A list of suitable solvents which can be employed and which is not meant to be limiting in any way, includes, for example:

xylene;
1,2-dichloroethylene;
iodoethane;
2-chloropropane;
1-iodo-2-methylpropane;
chlorobenzene;
carbon tetrachloride;
trans-1,2-dichloroethylene;
3-iodopropene;
1-chloro-2-methyl-1-propene;
isobutylnitrate;
1,1-dimethoxyethane; and benzene;
chloroform;
1,2-dichloroethane,
1,2-dichloropropane;
1-chlorobutane;
1,2-dimethoxyethane;
toluene;
cis-1,2-dichloroethylene;
bromoethane;
1-chloropropane;
1-chloro-2-methylpropane;
decane.

The alkali metal base reacts very quickly with the unsaturated fatty acid to produce the desired alkali metal carboxylic acid salt even at low temperatures. The exact temperature to employ will depend on the activity of the unsaturated fatty acid and alkali metal base. Suitable temperatures include those between 0°C. and 200°C., with temperatures between 20°C. and 100°C. being normally satisfactory, and temperatures between 20° and 40°C. being preferred.

The upper reaction temperature in the first stage is limited by the boiling point of the solvent unless increased pressures are employed. Increased pressures can be employed if desired but show no advantage over atmospheric operation. The upper temperature is therefore limited by that temperature wherein the solvent vaporizes since it is necessary to maintain the solvent in the liquid phase. It is noted, however, that the reaction of the alkali metal base with the unsaturated fatty acid is an exothermic reaction and suitable means, such as cooling coils, can be added to control the temperature of the first stage of the reaction to the desired level. The amount of cooling required will, of course, be proportional to the rate of addition, for example, of the alkali metal hydroxide solution to the mixture of solvent and unsaturated fatty acids. The reaction pressure is not critical but must be sufficient to maintain the unsaturated fatty acid and solvent in the liquid phase. Atmospheric pressure is generally preferred for reasons of economy, however, pressures as low as 1 mm of Hg. to as high as 100 psi can be employed. It may also be desirable to remove the water of reaction substantially as quickly as it is formed as an azeotrope with the above-defined solvent. Atmospheric pressure or below is preferred for this type of operation.

The manner of admixing the unsaturated fatty acid, alkali metal base and solvent is not critical. Usually the solvent and acid are admixed and the alkali metal base, in solution, is added dropwise continuously through the course of the reaction or in incremental portions or slugs during the reaction. It is not preferred to add all of the alkali metal base initially due to the heat of reaction developed which, as noted above, is difficult to control.

The reaction time for the first stage in the reaction is not critical and will vary depending on the exact temperature employed, but should be long enough to allow for the formation of the desired alkali metal acid salt. Reaction is very fast, however, even at the low temperatures of 0°C. and reaction times are generally on the order of one minute to 60 minutes, and more usually between five minutes and 15 minutes. If desired, a polymerization inhibitor, such as an amine, substituted phenol, or quinone, can be added to the reaction mixture to inhibit the polymerization of the acid or solvent. Sufficient mixing should be provided to insure adequate and uniform temperature control and contacting throughout the reaction zone.

After the formation of the desired alkali metal acid salt, the water is removed from the reaction mixture by any suitable means. One suitable means is to increase the temperature of the admixture of the alkali metal acid salt, solvent and water to allow for the removal of a water-solvent azeotrope at atmospheric pressure or under a vacuum, i.e. from one mm of Hg. to 760 mm of Hg. This temperature is usually between 95° and 115°C. at atmospheric pressure (760 mm Hg.). The water-solvent azeotrope can be treated in any suitable manner to recover the solvent and return it to the reaction if desired. As noted above, it is preferred that the solvent employed be substantially insoluble with the water so that it can be physically and easily separated from its azeotrope with water by decantation. The water of reaction can be removed substantially as quickly as it is formed, if desired. By operating in this manner, the reaction time in the first stage is reduced in accordance with the laws of mass action and, in addition, a second separate separation step is not required to remove the water before the addition of the epichlorohydrin and catalyst, as noted below.

When the reaction mixture from the first stage is substantially dry, which is shown by any suitable means, such as by the fact that only substantially pure solvent is removed overhead, i.e., no water is observed to form as a separate phase from the overhead product upon standing, the alklai metal salt formed in the first stage is then ready for further reaction with epichlorohydrin to form the desired glycidyl esters. Optionally, and preferably, a portion of the solvent used in the first stage can be removed from the first stage reaction product in order to reduce the reactor volume occupied by the solvent since its only function is to serve as a means of maintaining the alkali metal salt in a slurry suspension in the reactor, i.e., to prevent the salt from going to dryness and forming a hard cake or as a means of transporting the alkali metal salt from a first reaction zone to a second reaction zone, if such transportation is desired. Thus, both the first and second stage reactions or reaction zones may occur in a single reactor vessel or several reactor vessels can be provided with means for intermediate water removal and transportation. Suitably, from five to 95 weight percent, preferably from 50 to 95 weight percent, of the solvent form the first stage reaction product is removed before the first reaction product is further treated.

The slurry product from the first reaction zone which consists of the alkali metal salt admixed with or suspended in at least a portion of the solvent used in the first reaction zone is then contacted with a solid particulate drying agent which is free of halogen atoms. Any solid particulate drying agent which is free of halogen atoms can suitably be employed. By "particulate" is meant in a subdivided form, the exact size of which is not critical. The drying agent can be in the form of pellets, spheroids, granules or other shapes, the purpose of particulation being merely to aid in the contact between the first reaction zone product and the drying agent. Suitable drying agents, which are not meant to be limiting, include those which remove water by physical absorption or adsorption techniques such as silica gel and natural or synthetic zeolites; solid drying agents which remove water by chemical reaction to form hydroxides, such as calcium oxide; or solid drying agents which chemically combine with water to form hydrates, such as magnesium sulfate. The drying agents, after the desired contact with the first reaction zone product, are suitably removed before the first reaction zone product is contacted with epichlorohydrin in a second reaction zone to form the desired glycidyl ester. The removal of a solid particulate drying agent from a slurry of an alkali metal salt in a solvent is difficult and it is preferred the drying agent remain in the second stage reaction and be recovered together with the solid alkali metal chloride salt by-product from the second reaction zone or stage. It has been found, however, that only certain types of drying agents can, optionally, remain in the second reaction zone during the formation of the desired glycidyl ester without any adverse effects. Those drying agents which can optionally remain in the second reaction zone include (1) those which chemically react with water to form hydroxides; (2) those which chemically combine with water to form hydrates or higher hydrates; or (3) those which absorb water internally, such as natural or synthetic zeolites having an average pore diameter of less than about six °A.

One preferred group of drying agents are those which chemically react with water to form hydroxides and can be represented by the general formula:

$$Me_yO$$

where Me is an alkali metal selected from the group consisting of sodium or potassium or an alkaline earth metal selected from the group consisting of magnesium, calcium, strontium or barium; and y is one or two.

Suitable alkali and alkaline earth metal oxide drying agents include calcium oxide, barium oxide, strontium oxide and sodium oxide.

A second preferred class of drying agents are the alkali or alkaline earth metal sulfates which can be represented by the general formula:

$$Me_ySO_4$$

where Me and y have the same meaning as defined above. These alkali or alkaline earth mmetal sulfates chemically combine with water to form hydrates, and thus any hydrated form of the alkali or alkaline earth metal sulfate can also be employed so long as the hydrate is capable of forming a higher hydrate. Suitable alkali or alkaline earth metal sulfates or hydrates thereof include, but are not limited to, anhydrous magnesium sulfate, calcium sulfate, sodium sulfate or $MgSO_4 \cdot H_2O$.

The third class of preferred drying agents include the natural or synthetic zeolites having an average pore diameter of less than six °A. The most preferred drying agents in this class are the commercially available synthetic zeolites known as molecular sieves having an average pore diameter of either four or five °A. Larger average pore diameter zeolites can be employed but must be removed prior to the second stage reaction.

Well-known drying agents containing halogen atoms such as calcium chloride are undesirable for use in the process of this invention since they release a hydrogen halide upon chemical combination with water, and this hydrogen halide adversely interferes with the reactants to form unwanted side reaction products. While it is not certain, it is believed that those drying agents which physically adsorb water on their surfaces, such as silica gel, are undesirable when left in the second stage reaction since the water is effectively not removed from contact with the reactants. Small diameter sieves are effective although they chemically contain silica in their structure because they effectively remove the water from the reactants by adsorbing the water into the internal structure of the sieves while excluding the reactants and catalyst.

The amount of the solid particulate drying agent will vary depending on the type of drying agent and on the amount of solvent which is left in the first stage reaction product. The weight ratio of drying agent to the first stage reaction product being treated can broadly be from 0.01:1 to 10:1 or more but, usually, weight ratios on the order of 0.05:1 to 0.6:1 are satisfactory. The amount of drying agent is considerably reduced therefore by employing the preferred procedure of removing the bulk of the solvent from the first stage reaction product before it is contacted with the drying agent. The time and conditions for the contacting should be such as to allow the drying agent to perform its function of reacting or adsorbing the water which is present in the product from the first reaction zone. Preferably the contacting is done at temperatures from 10° to 100°C., usually a temperature from 20° to 70°C., and for times which can suitably vary from ten minutes to two hours or longer.

If the drying agent is to be removed or even partially removed it can be achieved by any suitable means such as selective sieving of the finely divided alkali metal salt from the particulate but coarser drying agent. Selective centrifugation may also be employed. As noted above, however, it is preferred that the drying agent can be chosen such that it need not be removed prior to the reaction to form the glycidyl ester.

The fist reaction zone product in the optional presence of the drying agents as defined above is then contacted in a second reaction zone or stage with dry epichlorohydrin under substantially anhydrous conditions to form the desired glycidyl ester. As noted above, the second reaction zone or stage may be in the same or a different reactor vessel from the first reaction zone or stage.

The epichlorohydrin should be as scrupulously dry as possible. To this end, it is preferable to not only redistill commercially available epichlorohydrin just prior to use in the subject reaction, but to contact the epichlorohydrin with a suitable drying agent such as natural or synthetic zeolites (molecular sieves) just prior to use to further reduce the water content, preferably to a water content of less than 10 ppm.

The reaction temperature in the second stage is suitably maintained from about 50° to about 100°C. and is preferably maintained from about 60° to 80°C., with the optimum temperature being about 70°C. The use of reaction temperatures above 100°C. is undesirable because a by-product is formed, the exact nature of which is unknown, but it is known that the by-product interferes with the separation of the epichlorohydrin from the desired glycidyl ester.

The reaction pressure in the second stage is not critical but should be such as to maintain the reactants in the liquid phase. Atmospheric pressure is preferred, but pressures within the range given for stage one above can also be successfully employed here.

The reaction between the alkali metal acid salt and the epichlorohydrin to form the desired glycidyl ester can be promoted thermally within the temperature range defined above. The thermal reaction is slow and is preferably promoted by the presence of a catalyst, the exact nature of which is not the essence of this invention. Thus, any catalytic material well known in the art can be employed to promote the reaction between epichlorohydrin and the alkali metal acid salt.

One class of catalytic materials which are preferred to promote the reaction of the alkali metal acid salt with epichlorohydrin are the quaternary ammonium halides. Preferred quaternary ammonium halides are represented by the general Formula VI below:

FORMULA VI

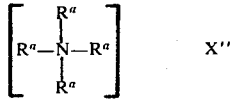

where N is nitrogen; X'' is chlorine or bromine; and R<sup>a</sup> is an unsubstituted hydrocarbon radical having between one and 12 carbon atoms, such as an alkyl, cycloalkyl, aryl, alkaryl, aralkyl and the like radicals.

Examples of suitable salts include, among others:
benzyltrimethylammonium chloride;
benzyltrimethylammonium bromide;
cyclohexyltrimethylammonium bromide;
phenotrioctylammonium bromide;
tetrabutylammonium chloride;
tetraoctylammonium chloride; and
tetramethylammonium bromide.

Other suitable catalytic materials include the tertiary amines, such as are defined in U.S. Pat. No. 3,075,999.

The amount of the catalyst to be used in the process may vary over a considerable range depending on the type of catalyst employed. Generally, the quaternary ammonium halides will be employed in amounts varying from about 0.01 percent to five percent by weight of the alkali metal acid salt reactant. Preferred amounts vary from about 0.01 percent to about three percent by weight of the alkali metal acid salt.

The time necessary to effectuate the reaction between the alkali metal acid salt and the epichlorohydrin can vary between about ten minutes and ten hours or more. The usual reaction times when a catalyst is employed are between one and eight hours, preferably between two and six hours, with the longer reaction times being required at the lower temperatures and with the lower catalyst concentrations.

The alkali metal acid salt and the epichlorohydrin react to form the desired glycidyl ester in accordance with the following equation:

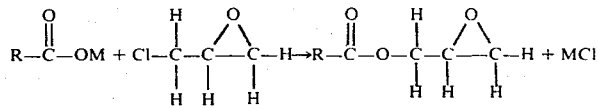

where R and M have the significance given above. Stoichiometrically, one mole of epichlorohydrin is required for each mole of the alkali metal salt. It is preferred, however, to employ much higher molar ratios of epichlorohydrin to the alkali metal acid salt in order to obtain high yields of the desired glycidyl ester. Thus the molar ratio of epichlorohydrin to salt is preferably from about 3:1 to 100:1 or more and is more preferably from 8:1 to 16:1. Obviously, the amounts of epichlorohydrin above the stoichiometric amounts function as a solvent and in some manner to inhibit the formation of undesired side reaction products.

It has additionally been found that the molar ratio of epichlorohydrin to the solvent which is employed in reaction zone one and which is carried over into reaction zone two must be above about 2:1 in order to produce the high yields of the desired glycidyl esters. Preferably the epichlorohydrin to solvent molar ratio in the second reaction zone or stage should be from 2:1 to 20:1, although ratios as high as 100:1 or higher can obviously be employed. It is important that the epichlorohydrin to salt molar ratio and the epichlorohydrin to solvent molar ratios be within the above-defined ranges simultaneously in order to obtain the high yields of glycidyl esters.

After the formation of the desired glycidyl ester, the total reaction product is treated to separate the unreacted epichlorohydrin from the glycidyl ester reaction product. Any suitable means can be used to effectuate the separation, such as distillation. It has been found that if the content of chlorohydrin ester

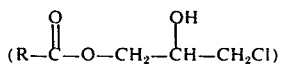

by-product is above about six weight percent of the reaction product, that conventional distillation is not recommended due to high losses of glycidyl ester during distillation. It appears the glycidyl ester in some manner polymerizes during fractionation. Distillation under high vacuum and in the presence of polymerization inhibitors such as those mentioned above still results in the production of a high boiling material, and thus some of the valuable glycidyl ester is lost.

One successful method for the separation of epichlorohydrin from a glycidyl ester, such as glycidyl methacrylate, in the presence of the chlorohydrin ester

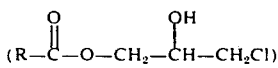

in amounts of about six weight percent and above has been to insert the admixture of the epichlorohydrin, chlorohydrin ester and glycidyl ester to the middle section of a packed column maintained at a temperature between 25° and 100°C. under a reduced pressure of from about one to about 100 millimeters of mercury while simultaneously passing an inert gas, such as nitrogen, methane, argon, etc., into the bottom of the column and out the top. The conditions in the column are such that the epichlorohydrin is vaporized and the glycidyl and chlorohydrin esters remain liquid. The epichlorohydrin is swept from the column out the top along with the inert gas entering at the bottom of the column. The glycidyl ester, such as glycidyl methacrylate, being a liquid, passes downwardly as a thin film where it is contacted by the inert gas to remove any traces of epichlorohydrin finding their way into the bottom section of the column. The liquid glycidyl ester leaving the bottom of the column enters a cold pot maintained at a temperature of about 0°C. in order to reduce any possibility of polymerization of the glycidyl methacrylate. The purity of the glycidyl ester using this procedure is excellent, being on the order of 97 percent. If the content of chlorohydrin ester is less than about six weight percent of the reaction product, conventional distillation procedures can be employed.

The following invention will be further described with reference to the following experimental work.

EXAMPLE 1

In the run for this example, 300 grams of heptane and 43 grams (0.5 mole) of methacrylate acid were admixed at ambient conditions in a one liter four necked resin kettle equipped with a Dean-Stark trap; a cold water condenser; a stirring rod; thermometer; means for maintaining a nitrogen atmosphere and means for heating. A solution of 33 grams (0.59 mole) of potassium hydroxide in 20 cc's of water were then added to this first reaction zone in 10 cc amounts over a 15 minute period at 27°C. The temperature was incresed to 99°C. and the water was azeotroped off over a period of 5½ hours at atmospheric pressure (A total of about 30 cc's of water was removed.). The azeotrope was condensed and separated into a lower water phase and an upper organic phase. The organic phase was recycled until the reaction mixture was substantially dry as shown by an increase in temperature and by no further water separation in the condenser. The temperature was increased to remove 240 cc's of heptane overhead.

The reaction temperature was lowered to 60°C. and 25 grams of a synthetic zeolite (Linde molecular sieves) having an average pore diameter of four °A. were added and the mixture was stirred for one hour.

In a second reaction zone or stage, and without prior separation of the zeolite, 500 grams of dry epichlorohydrin (redistilled and passed through a column of 4°A. molecular sieves) were added and the temperature was increased to 90°C. at which point 1.2 grams of benzyltrimethylammonium chloride was added as a catalyst. The reaction continued for two hours. The epichlorohydrin to alkali metal salt mole ratio in this second stage was 11:1 while the epichlorohydrin to heptane mole ratio was 9:1. The reaction mixture was filtered to remove solids which were washed with dry epichlorohydrin and the wash liquid was added to the filtrate.

Analysis of the product showed the yield of glycidyl methacrylate was 100 mole percent of the theoretical amount possible based on the 0.5 mole of alkali metal salt. The product analyzed 95.3 weight percent glycidyl methacrylate; 1.9 weight percent 1,3-dichloropropanol-2; and 2.8 weight percent of other impurities, primarily the chlorohydrin ester.

Analyses in this and later examples were performed by gas liquid chromatography using a four foot long, 1/16 inch column packed with ten percent Carbowax 20 M on Aeropak 30 using a helium pressure of 65 pounds with a dual column. The temperature program was as follows: (1) an initial temperature of 75°C. for two minutes; (2) an increse of about 20°C. in one minute and holding for two minutes; (3) increasing the temperature at about 15°C. per minute for six minutes, holding for one minute and (4) increasing the temperature at about 10°C. per minute for seven minutes and holding for 25 minutes at a final temperature of about 200°C. The injector temperature was 225°C. and the detector oven temperature was 230°C.

Substantially the same results are obtained when acrylic acid is used in place of methacrylic acid to produce glycidyl acrylate.

EXAMPLE 2

Example 1 was repeated except anhydrous magnesium sulfate ($MgSO_4$) was used in place of the 4°A. molecular sieves to treat the alkali metal salt slurry from the first reaction zone and 255 cc's of heptane were removed from the reaction product from step one (85 weight percent removed), resulting in an epichlorohydrin to heptane mole ratio in the second stage of about 12:1.

The yield of glycidyl methacrylate was 97.7 mole percent of the theoretical amount possible based on the 0.5 mole of alkali metal salt reacted with the epichlorohydrin in the second step. The product analyzed 92.5 weight percent glycidyl methacrylate; 3.7 weight percent of the 1,3-dichloropropanol-2 and 3.8 weight percent of other impurities, primarily the chlorohydrin ester.

EXAMPLE 3

Example 2 was repeated except calcium sulfate ($CaSO_4$) was used in place of the magnesium sulfate.

The yield of glycidyl methacrylate on the same basis was 98.9 mole percent and the product analyzed 94.4 weight percent glycidyl methacrylate; 1.8 weight percent 1,3-dichloropropanol-2 and 3.8 weight percent of other impurities, primarily the chlorohydrin ester.

EXAMPLE 4

Example 1 was repeated except calcium oxide (CaO) was used in place of the 4°A. molecular sieves to treat the alkali metal salt slurry from the first reaction zone and 282 cc's of heptane were removed from the reaction product from step one (94 weight percent removed), resulting in an epichlorohydrin to heptane mole ratio in the second stage of about 30:1.

The yield of glycidyl methacrylate on the same basis as the examples above was 94.4 mole percent and the product analyzed 96.5 weight percent glycidyl methacrylate; 0.4 weight percent 1,3-dichloropropanol-2; and 3.1 weight percent of other impurities, primarily the chlorohydrin ester.

A comparison of Examples 1–4 shows that various drying agents can be employed in the process of this invention to result in substantially theoretical yields of the desired glycidyl ester with very little by-product formation.

EXAMPLE 5

Example 2 was repeated except no heptane was removed between stages one and two and the second stage was operated for four hours at 97°C. The epichlorohydrin to heptane mole ratio was reduced to about 2:1.

The yield of glycidyl methacrylate on the same basis as in Example 2 was 89.5 mole percent and the product analyzed 91.4 weight percent glycidyl methacrylate; 4.6 weight percent 1,3-dichloropropanol-2; and 4.0 weight percent of other impurities, primarily the chlorohydrin ester.

A comparison of Examples 2 and 5 shows that it is preferred to remove at least a portion of the solvent from stage one, preferably to remove from 50 to 95 weight percent of the solvent from stage one, to obtain improved yields and purity of product.

EXAMPLE 6

An aqueous solution of 33 grams of potassium hydroxide (0.59 mole) in 20 grams of water (1.1 mole) was added gradually with rapid stirring over a period of ten minutes. The temperature was maintained between 26° and 41°C. Stirring was continued and the reaction vessel temperature was increased to remove overhead a water-1,2-dichloroethane azeotrope boiling at 82°C. The azeotrope was condensed and the azeotrope separated into an upper water phase and a lower organic phase. The bottom layer of solvent was recycled to the reaction vessel until the reaction mixture was substantially dry as shown by an increase in temperature and by no further water separation in the condenser. Pure solvent was then distilled off until the reaction mixture became a thick slurry which was still pumpable and in which the potassium methacrylate was suspended.

694 grams of distilled and molecular sieve dried epichlorohydrin (7.5 moles) was added to the slurry of potassium methacrylate. The reaction temperature was then lined out at 70°C. and 1.16 grams (0.006 moles) of benzyltrimethylammonium chloride were added. Reaction was continued for five hours, after which the reaction mixture was filtered to remove the potassium chloride salts. The salts were washed with 100 grams of epichlorohydrin and the wash was added to the filtrate.

The combined liquid was analyzed as in Example 1. The yield of glycidyl methacrylate on the same basis as the above examples was 71.4 mole percent and the product analyzed 93.2 weight percent glycidyl methacrylate; 3.7 weight percent 1,3-dichloropropanol-2; and 3.1 weight percent of other impurities, primarily the chlorohydrin ester.

The epichlorohydrin to solvent mole ratio in Example 6 was about 1.9:1.

A comparison of Examples 5 and 6 shows that there is a substantial decrease in the yield of glycidyl methacrylate (89.5 mole percent for Example 5 to 71.4 mole percent for Example 6) when the use of a drying agent as taught by this invention is omitted.

EXAMPLE 7

Example 4 was repeated except calcium chloride was used in place of the calcium oxide and sufficient heptane was removed from stage one so that the epichlorohydrin to heptane mole ratio in stage two was 15:1.

The yield of glycidyl methacrylate on the same basis as the examples above was only 54.6 mole percent and the product analyzed 77.4 weight percent glycidyl methacrylate; 16.5 weight percent 1,3-dichloropropanol-2; and 6.1 weight percent of other impurities, primarily the chlorohydrin ester.

EXAMPLE 8

Example 2 was repeated except No. 70 mesh silica gel (320 m$^2$/gram; 10 mesh size and greater, purchased from Davison Chemical Company and activated by heating to 1000°F.) were used in place of the anhydrous $MgSO_4$.

The yield of glycidyl methacrylate on the same basis as the examples above was only 65.9 mole percent and the product analyzed 78.2 weight percent glycidyl methacrylate; 2.7 weight percent 1,3-dichloropropanol-2; and 19.1 weight percent other impurities, primarily the chlorohydrin ester.

EXAMPLE 9

Example 8 was repeated except most (but not quite all, i.e., about 0.5 weight percent removed) of the silica gel was removed before the addition of the epichlorohydrin.

The yield of glycidyl methacrylate increased to 82.7 mole percent and the product analyzed 90.7 weight percent glycidyl methacrylate; 4.7 weight percent 1,3-dichloropropanol-2; and 4.5 weight percent of other impurities, primarily the chlorohydrin ester.

A comparison of Examples 7 and 8 with the earlier examples shows the use of halogen containing drying agents ($CaCl_2$) and drying agents which physically adsorb water, such as silica gel, result in decreased yields and purity of product. Example 9 shows that removal of the silica gel before the second stage reaction results in an increase in yield and purity of product.

EXAMPLE 10

Example 1 was repeated except the molecular sieves were removed from the first stage reaction product before the epichlorohydrin was added.

The yield of glycidyl methacrylate on the same basis as Example 1 was 97.7 mole percent and the product analyzed 97.6 weight percent glycidyl methacrylate; 1.0 weight percent 1,3-dichloropropanol-2; and 1.3 weight percent other impurities, primarily the chlorohydrin ester.

A comparison of Examples 1 and 10 shows that substantially the same results are obtained either in the presence or absence of the 4°A. molecular sieve in stage two.

EXAMPLE 11

Example 2 was repeated except the water was not removed from the first stage reaction product. The yield of glycidyl methacrylate decreased to 45.5 mole percent and the weight percent glycidyl methacrylate in the product was reduced to 67.8 with a corresponding increase in side reaction products.

EXAMPLE 12

Example 11 was repeated except the molecular sieves used in Example 1 were used in place of the $MgSO_4$. Substantially the same results were obtained as in Example 11, showing that removal of the water from the first stage reaction product by azeotropic distillation is essential in the process of this invention. Resort may be had to such variations and modifications as fall within the spirit of the invention and the scope of the appended claims.

I claim:

1. A process for the preparation of glycidyl methacrylate which comprises:
   reacting methacrylic acid with an alkali metal base to form an alkali metal salt of said acid and water in a first reaction zone in the presence of an epoxide-free solvent which will azeotrope with water;
   removing substantially all of the water from said first reaction zone by azeotropic distillation and from 50 to 95 weight percent of said solvent to form a first reaction zone product slurry;
   contacting said first reaction zone product slurry in a second reaction zone with a solid particulate drying agent free of halogen atoms, said drying agent being such that it either reacts with water to form an hydroxide or hydrate or is a zeolite having an average pore diameter of less than six degrees Angstrom;
   and thereafter reacting said slurry in the presence of said drying agent in a second reaction zone with dry epichlorohydrin under substantially anhydrous conditions to form the desired glycidyl methacrylate.

2. A process for the preparation of glycidyl methacrylate which comprises:
   reacting methacrylic acid with an alkali metal base to form an alkali metal salt of said acid and water in a first reaction zone in the presence of an epoxide-free solvent which will azeotrope with water;
   removing substantially all of the water from said first reaction zone by azeotropic distillation and from 50 to 95 weight percent of said solvent to form a first reaction zone product slurry;
   contacting said first reaction zone product slurry with a solid particulate zeolitic drying agent free of halogen atoms and having an average pore diameter of less than six degrees Angstrom;
   and thereafter reacting said slurry in the absence of said drying agent in a second reaction zone with dry epichlorohydrin under substantially anhydrous conditions to form the desired glycidyl methacrylate.

* * * * *

UNITED STATES PATENT AND TRADEMARK OFFICE
CERTIFICATE OF CORRECTION

PATENT NO. : 3,957,831
DATED : May 18, 1976
INVENTOR(S) : William J. Heilman

It is certified that error appears in the above-identified patent and that said Letters Patent are hereby corrected as shown below:

Col. 2, line 24 - "or" should be --of--;
Col. 2, line 25 - "tht" should be --that--;
Col. 2, line 33 - "solvent" should be --unsaturated--;
Col. 3, line 14 - "two to" should be --where--;
Col. 6, line 63 - after "reaction" insert --zone--.

Signed and Sealed this

Seventh Day of September 1976

[SEAL]

Attest:

RUTH C. MASON
*Attesting Officer*

C. MARSHALL DANN
*Commissioner of Patents and Trademarks*